US00PP10176P

United States Patent [19]

Zaiger et al.

[11] Patent Number: Plant 10,176

[45] Date of Patent: Jan. 6, 1998

[54] PEACH TREE "SWEET DREAM"

[76] Inventors: Chris Floyd Zaiger, 629 Grimes Ave.; Gary Neil Zaiger, 1907 Elm Ave.; Leith Marie Gardner, 1207 Grimes Ave.; Grant Gene Zaiger, 4005 California Ave., all of Modesto, Calif. 95358

[21] Appl. No.: 738,187

[22] Filed: Oct. 28, 1996

[51] Int. Cl.[6] ..... A01H 5/00

[52] U.S. Cl. ..... Plt./43.1

[58] Field of Search ..... Plt./43.1

*Primary Examiner*—James R. Feyrer

[57] ABSTRACT

A new and distinct variety of peach, *Prunus persica*, tree. Its novelty consists of the following unique combination. of features that are desirable in a new peach variety:

1. Produces fruit with mild, sweet, subacid flavor with very good eating quality.
2. Heavy and regular production of large size fruit.
3. Fruit with firm flesh, good handling and shipping quality.
4. Fruit having a high degree of attractive red skin color.
5. Vigorous, upright growth habit.
6. Fruit holding firm on the tree 10 to 14 days after maturity (shipping ripe).
7. Relatively uniform maturity of fruit throughout the tree.

1 Drawing Sheet

ORIGIN OF THE VARIETY

The new and distinct variety of peach tree was originated by us in the experimental orchard located near Modesto, Calif. After the seed was collected and cleaned for planting, the identification tag became lost and the parentage was recorded as Misc. Peach. From the similarity in characteristics of the tree and its fruit we believe it to possibly be open pollinated Sweet Gem Peach (U.S. Plant Pat. No. 7,952) parentage. A large group of these seedlings labeled Misc. Peach were grown and maintained under careful observation by us, during which time one such seedling, which is of the present variety, exhibited especially desirable fruit characteristics and was selected for asexual reproduction and commercialization.

ASEXUAL REPRODUCTION OF THE VARIETY

The present new and distinct variety of peach tree was asexually reproduced by budding, as performed by us in our experimental orchard located near Modesto, Calif., which shows that all characteristics of the tree and its fruit are established and transmitted through succeeding asexual propagations.

SUMMARY OF THE VARIETY

The present new variety of peach tree is of large size, vigorous, upright growth and a heavy and regular bearer of large, firm, yellow flesh, clingstone fruit with very good flavor and eating quality. The fruit is further characterized by holding firm on the tree 10 to 14 days after shipping ripe, having good handling and shipping quality, being relatively uniform in size throughout the tree and having a high degree of attractive red skin color. The present variety of peach tree when compared to the subacid Sweet Gem Peach (U.S. Plant Pat. No. 7,952) is similar in flavor and eating quality, has less apical point and is approximately 35 days later in maturity.

DESCRIPTION OF THE PHOTOGRAPH

The accompanying photographic illustration shows typical specimens of the foliage and fruit of the present new variety of peach tree. The upper and lower surface of the leaves being illustrated with an exterior and sectional view of the fruit divided in the suture plane to reveal flesh coloration, pit cavity and a stone remaining in place. The photograph was taken shortly after the fruit was picked at maturity (firm ripe) and the colors are as nearly true as is reasonably possible in a color representation of this type.

DESCRIPTION OF THE VARIETY

The following is a detailed botanical description of the new peach tree, its flowers, foliage and fruit as based on observations of specimens grown in our experimental orchard near Modesto, Calif. with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Upright.
- *Density.*—Medium dense.
- *Productivity.*—Productive.
- *Bearing.*—Regular.

Trunk:
- *Size.*—Large.
- *Texture.*—Medium shaggy.
- *Color.*—Brown to soot brown (5-E-5 ) to (5-F-5 ).

Branches:
- *Size.*—Medium.
- *Texture.*—Smooth to medium rough, varies with maturity.
- *Lenticels.*—Numerous. Large size.
- *Color.*—Light brown to brown (5-D-6 ) to (5-E-8 ).

Leaves:
- *Size.*—Large. Average length 6½". Average width 1⅝".
- *Texture.*—Smooth.
- *Thickness.*—Medium.
- *Margin.*—Crenate.
- *Form.*—Lanceolate, pointed.
- *Petiole.*—Medium length. Medium thickness.
- *Glands.*—Number varies from 1 to 5. Average number 3. Medium to large size. Reniform. Located on base of leaf blade and upper portion of the petiole.
- *Color.*—Upper surface—green to dark green (29-F-7) to (29-F-8). Lower surface—grayish green to green (29-E-7) to (29-E-8).

Flower buds:
*Size.*—Large.
*Form.*—Plump.
*Pubescence.*—Pubescent.
Flowers:
*Size.*—Large, showy.
*Blooming Period.*—Date of first bloom: Mar. 4, 1994. Date of full bloom: Mar. 9, 1994.
*Pollen.*—Present.
*Color.*—Pink.
Fruit:
*Maturity when described.*—Shipping ripe.
*Date of first picking.*—Jul. 18, 1994.
*Date of last picking.*—Jul. 24, 1994.
*Size.*—Large. Average diameter axially 3¼". Average transversely in suture plane 3¼".
*Form.*—Nearly globose, varies from round to slightly flattened in suture plane.
*Suture.*—Shallow, extends from base to slightly beyond apex.
*Ventral surface.*—Rounded.
*Cavity.*—rounded, slightly elongated in suture plane. Average depth ⅝". Average breadth 1".
*Base.*—Retuse.
*Apex.*—Usually rounded, varies from round to very slight point.
Flesh:
*Ripens.*—Evenly.
*Texture.*—Firm.
*Fibers.*—Small, few, tender.
*Juice.*—Moderate.
*Aroma.*—Moderate.
*Amygdalin.*—Undetected.
*Flavor.*—Very good, mild, sweet, subacid.
*Eating quality.*—very good.
*Color.*—Light yellow to golden yellow (3-A-5) to (3-A-7). Pit cavity, yellow to grayish yellow (3-A-5) to (3-B-3) slight red staining from stone.
Skin:
*Thickness.*—Medium.
*Texture.*—Medium, tenacious to flesh.
*Tendency to crack.*—None.
*Down.*—Moderate amount. Short in length.
*Color.*—Yellow to golden yellow ground color (4-A-6) to (4-A-8). Overspread with red to crayfish red (9-B-8) to (9-C-8).
Stone:
*Type.*—Clingstone.
*Size.*—Large. Average length 1½". Average width 1⅛". Average thickness ⅞".
*form.*—Obovate.
*Base.*—Usually straight, varies from straight to rounded.
*Apex.*—Usually cuspidate, varies from cuspidate to rounded.
*Sides.*—Equal to unequal.
*Surface.*—Irregularly furrowed toward apex, pitted toward base.
*Tendency to split.*—None.
*color.*—Brownish red to reddish brown (9-C-8) to (9-D-8).
Use: Dessert.
*Market.*—local and long distance.
Shipping quality: Good.
Keeping Quality: Good.

The present new and distinct variety of peach tree, its flowers, foliage and fruit herein described may vary in slight detail due to climate, soil conditions and cultural practices under which the variety may be grown; the present description is that of the variety grown under the ecological conditions prevailing near Modesto, Calif.

We claim:

1. A present new and distinct variety of peach tree, substantially as illustrated and described, characterized by its large size, vigorous upright growth and being a productive and regular bearer of large size, yellow flesh, clingstone fruit; the fruit is further characterized by having a high degree of attractive red skin color, firm flesh with good handling and shipping quality and, having a mild, sweet, subacid flavor with very good eating quality and, in comparison to the subacid fruit of Sweet Gem Peach (U.S. Plant Pat. No. 7,952) the fruit is approximately 35 days later in maturity.

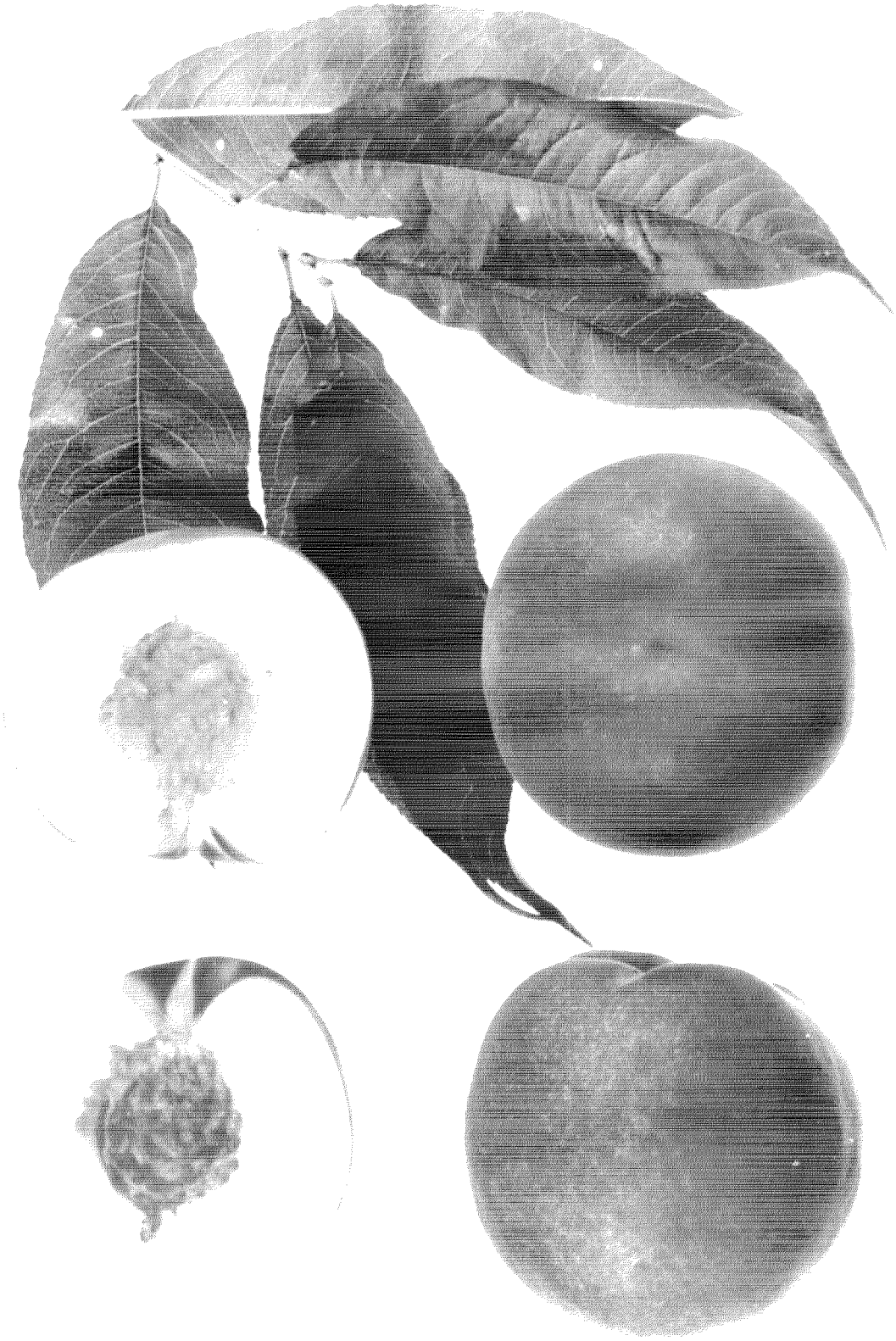

* * * * *